United States Patent [19]
Lin et al.

[11] Patent Number: 5,744,468
[45] Date of Patent: Apr. 28, 1998

[54] HYPOTENSIVE INTRAOCULAR PRESSURE ACTIVITY OF CLOZAPINE AND SULPIRIDE

[75] Inventors: Tong-Ho Lin, 7F-1, No.200, Sec.1, Fu-Hsing S.Rd., Taipei; Ing-Jun Chen, Kaohsiung, both of Taiwan

[73] Assignee: Tong-Ho Lin, Taipei, Taiwan

[21] Appl. No.: 736,010

[22] Filed: Oct. 23, 1996

[51] Int. Cl.$^6$ ............................ A61K 31/55; A61K 31/40
[52] U.S. Cl. ............................................ 514/220; 514/428
[58] Field of Search ...................................... 514/220, 428

[56] References Cited

U.S. PATENT DOCUMENTS

| | | | |
|---|---|---|---|
| 3,539,573 | 11/1970 | Schmutz et al. | 514/212 |
| 4,772,616 | 9/1988 | Chiou | 514/322 |
| 5,266,580 | 11/1993 | Chiou . | |
| 5,571,823 | 11/1996 | Stone et al. | 514/317 |

*Primary Examiner*—Raymond Henley, III
*Attorney, Agent, or Firm*—Beveridge, DeGrandi, Weilacher & Young, LLP

[57] ABSTRACT

This invention introduces a novel anti-glaucoma solution which comprises of Clozapine or Sulpiride and a pharmaceutical vehicle. This is the first time all the above agents have been prepared in ophthalmologic solutions, which will be able to decrease the IOP in animals.

19 Claims, 8 Drawing Sheets

Clozapine

Fig.1 (a)

Sulpiride

HYPOTENSIVE INTRAOCULAR PRESSURE ACTIVITY OF CLOZAPINE AND SULPIRIDE

INTRODUCTION

In C. Y. George's 1989 experiment, it was discovered that some dopamine receptor antagonists belonging to an antipsychotic drug were found to be able to reduce intraocular pressure(IOP) and increase the blood flow to the retina, choroid, iris and ciliary body in rabbits. According to Schizophrenia Bull, vol. 17, pp.263–309, 1991 by Meltzer H. Y., antipsychotic drugs can be generally divided into two categories. One is a typical antipsychotic drug which will produce side effects of parkinsonism and tarditive dyskinesia, the other an atypical antipsychotic which won't produce the above side effects. Antipsychotic drugs are usually categorized to be dopamine receptor antagonist.

In 1979 Drugs vol. 17 pp. 38–55, reported that a non selective β-adrenergic receptors L-timolol could treat patients with glaucoma in clinics. Therefore it was thought that β blocker drugs could lower the IOP in treating patients with glaucoma. Then in 1986 Inv. Ophthalmol. Vis. Sci. Vol. 27 reported that L-timolol couldn't improve parcipitation of retinopathy. This fact has led many investigators to search for a newer anti-glaucoma agent.

Recently subtype $D_{1A}$, $D_{1B}$, $D_{2A}$, $D_{2B}$, $D_3$, $D_4$ and $D_5$ have been separated out from a number of dopamine receptors with molecular cloning techniques in 1992 by Sibley D. R.(reported in Sci. Trends Pharmac. Vol. 13, pp. 61–69).

When daily doses of clozapine 30 mg/kg and sulpiride 100 mg/kg were given respectively to male Wistar rats, it was found after a long term observation that these drugs could up-regulate the mRNA levels in the dopamine $D_3$ receptor. Clozapine could also increase mRNA levels in the dopamine $D_{1B}$ levels, but could not in the $D_{1A}$ or $D_2$ receptors, as well as in aromatic amino acid decarboxylase, tyrosine hydroxylase or any other dopamine synthesizing enzymes. In contrast, sulpiride at a higher dose 100 mg/kg/day elicited a large increase in abundance of the mRNA coding in the dopamine $D_3$ receptor. In any case, neither the atypical antipsychtic drugs Sulpiride nor Clozapine was discovered to have a function of $D_3$ dopaminergic antagonists which was able to reduce IOP.

DETAILED DESCRIPTION OF THIS INVENTION

Summary of the Invention

Figure 1:
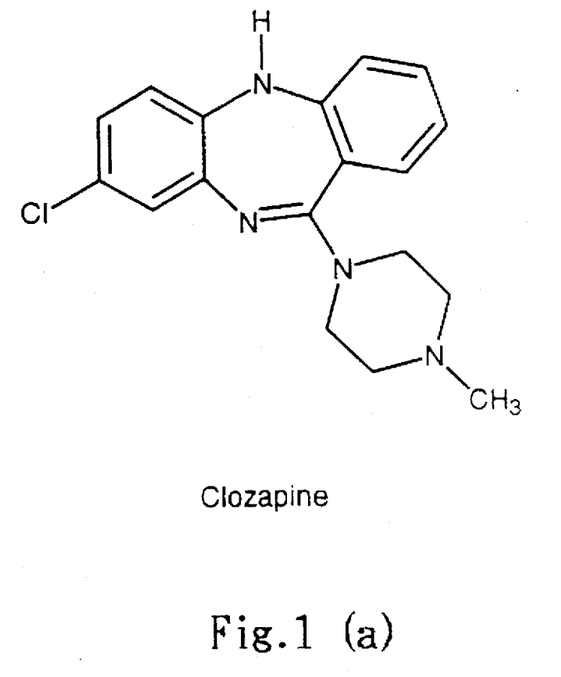
FIG. 1 is the chemical structure of (a) clozapine and (b) sulpiride.

The present invention is aimed at discovering a new anti-glaucoma agent. In FIG. 1 Clozapine and Sulpiride, which are known to belong to $D_3$ dopaminerqic antagonist, are for the first time prepared in an ophthalmologic solution to treat the IOP in animals.

According to Paul R. Buckland & Co's report in Neuropharmacology 1993 vol.32 pp901–907, the treatment of Antipsychotic drug was shown to be able to up-regulate the mRNA levels in dopamine $D_3$ receptor. Up till now, clozapine is still thought to be an ideal atypical antipsychotic drug not only because it has less side effects, but also because it is useful to patients who fail to be treated by other antipsychotic drugs.

The main purpose of this invention is to reveal a new anti-glaucoma ophthalmologic solution which comprises of the antipsychotic drug Clozapine or Sulpiride and a pharmaceutical vehicle.

Another purpose of this invention is to reveal a new treatment in the function of Clozapine and Sulpiride. They not only have their original antipsychotic activity, but they also comprise the activity to decrease the IOP of mammals. One of the two is clozapine, this is an important drug in treating parcipitation of retinopathy.

Clozapine and Sulpiride belong to the atypical antipsychotic drug, they have the activity to decrease the IOP of mammals.

Sulpiride at a higher concentration(20%) could also reveal a similar effect to that of Clozapine(0.5%). This indicates that it has a milder up-regulation of mRNA levels in dopamine $D_3$ receptor in the cells than Clozapine has. Thus dopamine $D_3$ is thought to be relevant to the ophthalmic system in the future.

According to the experiment it has been proved that Clozapine not only decreases IOP but has a vasodilatory effect. This activity shows Clozapine has the potential ability to increase the blood flow. It is an important drug in treating parcipitation of retinopathy.

I. Compositions Preparation Methods

This invention reveals a novel anti-glaucoma solution which comprises of clozapine or sulpiride and a pharmaceutically carrier. For treatment, various saline, diluents, lubricants, stabilizer and binders are added with clozapine and sulpiride. Alkaline mineral acid is used to adjust the pH balance to prepare ophthalmic ointment and solution.

In this invention Clozapine and Sulpiride have been used to prepare the ophthalmic ointment and solution. Both emulsified and non-emulsified clozapine had the same treatment result in decreasing IOP in animals. Mammals were mainly used in this experiment. The general dosage depends on the symptom. Usually for each person one to three drops each time, three times a day.

In general, Clozapine drop solution is prepared first by dissolving clozapine in 0.9% NaCl solution, and Sulpiride is mixed by propylene glycol. Then the pH balance is adjusted with mineral acid. Later a stabilizer or emulsed stabilizer is added. This invention reveals an anti-glaucoma medicinal combination which comprises of Clozapine and Sulpiride. It is optional to prepare a ophthalmic drop solution or ointment. Ophthalmic solution is made of NaCl, boric acid, alkaline mineral acid and sodium sulphate. Also alkaline is used to compose pH7.4 phosphate buffer. The alkaline mineral acids used were $Na_2HPO_4$ and $NaH_2PO_4$. If necessary, a stabilizer or fungicide could be added. Choose hydroxypropyl β cyclodextrin, carboxymethylcellulose to be the stabilizer; and chlorobutanol to be the fungicide. Usually choose non-irritant white Vaseline® (petroleum), mineral oil or water-free sheep oil to be the base ingredient of the ointment.

II. Pharmacological activity

The experiment method used to research the decreasing of IOP activity in clozapine and sulpiride followed the reports in Vareilles 1981, vol 13 pp72–79. New Zealand albino rabbits of either sex were used in the study. A 20% hypertonic saline solution was infused at the speed of 1 ml per min for 10 minutes through the marginal ear vein with an infusion pump. After dropping 0.5% alcaine eye drops in both eyes for one minute, Clozapine drop solution (50 µl, 0.5%) and vehicle drop solution(50 µl) were gradually instilled respectively.

Then the IOP of both eyes were measured with a Tono-Pen XL Tonometer (Mentor, Norwell, Mass.) at 30 minute and 10 minute intervals before the experiment. At the time of commencement, as well as at 10, 20, 40, 60, and 80 rain intervals measurements were taken, Then measurements were repeated at every 30 minute intervals. Identical experiments were repeated for another group of animals with emulsified Clozapine drop solution (50µl, 0.5%) and Sulpiride drop solution( 50 µl, 20%).

The IOP recovery curve acquired had shifted to the right and below the curve of the controlled group. It indicated that these drugs have the activity to decrease IOP.

Results

Figure 2:
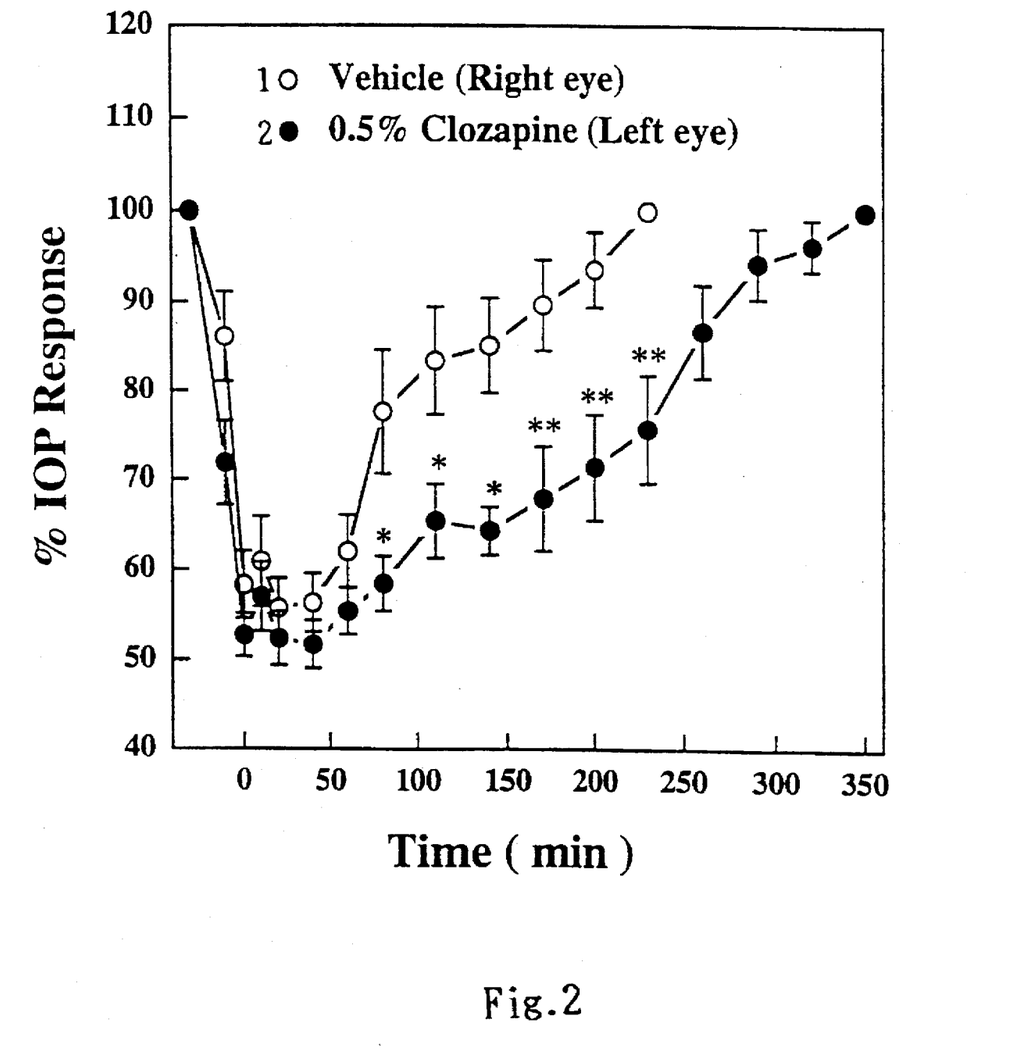
FIG. 2 is a graph showing that clozapine was able to decrease the intraocular pressure response in rabbits; 1. Vehicle (right eye); 2. 0.5% Clozapine (left eye).

IOP is considered to be the major factor which causes glaucoma, and drugs with activity of reducing IOP are considered to be able to treat glaucoma. As shown in FIG. 2, 0.5% Clozapine drop solution was able to decrease the IOP recovery time of rabbits. It inhibited the IOP response more than the control group.

Figure 3:
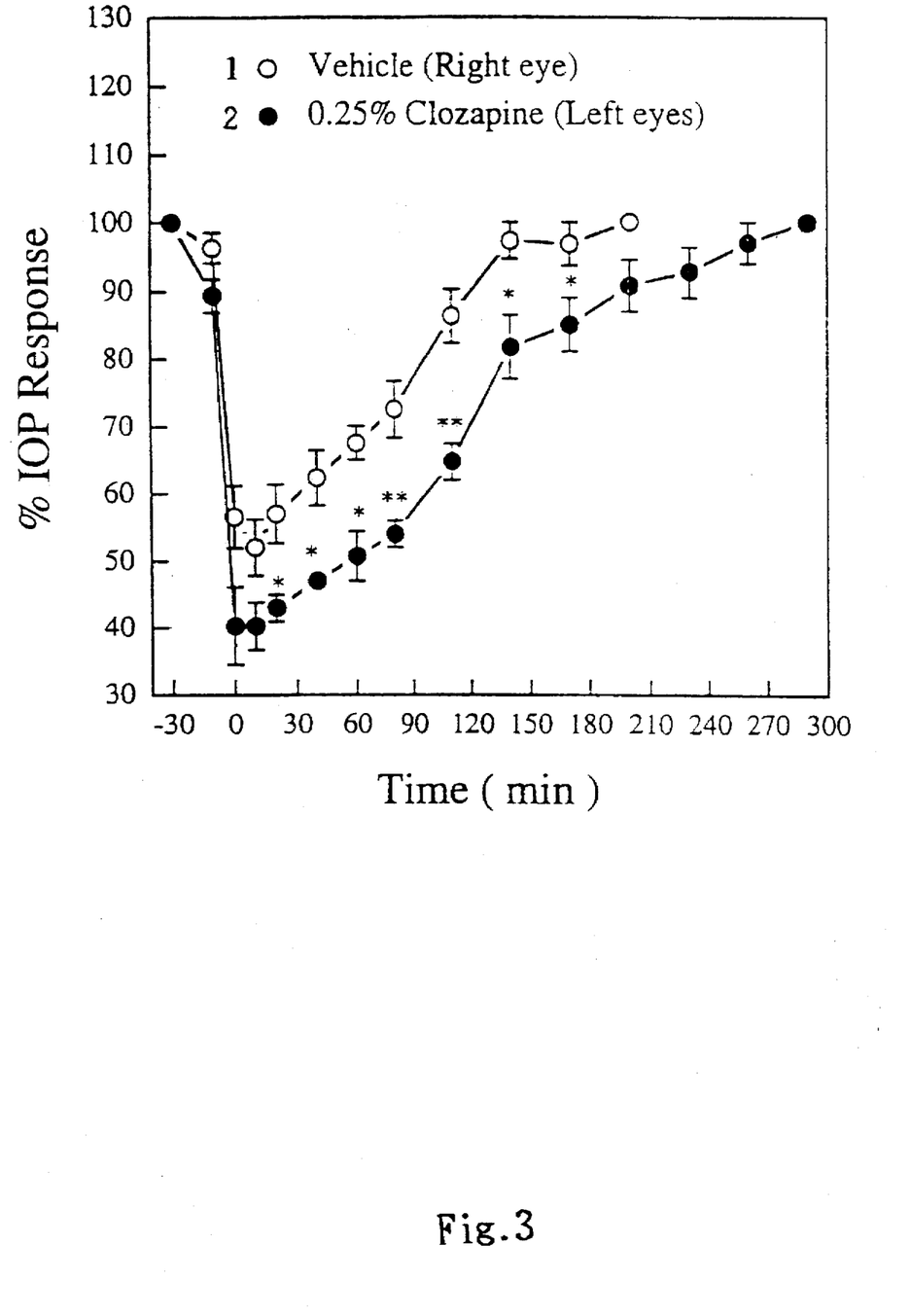
FIG. 3 is a graph showing that clozapine was able to decrease the intraocular pressure (IOP) in rabbits. The graph shows the effects of 0.25% clozapine in the rabbit IOP recovery model. Each point is the mean of 5 values and bars represent SEM. *:P<0.05; **:P<0.01 significantly different from the vehicle group. 1. Vehicle (right eye); 2. 0.25% Clozapine (left eye).
Figure 4:
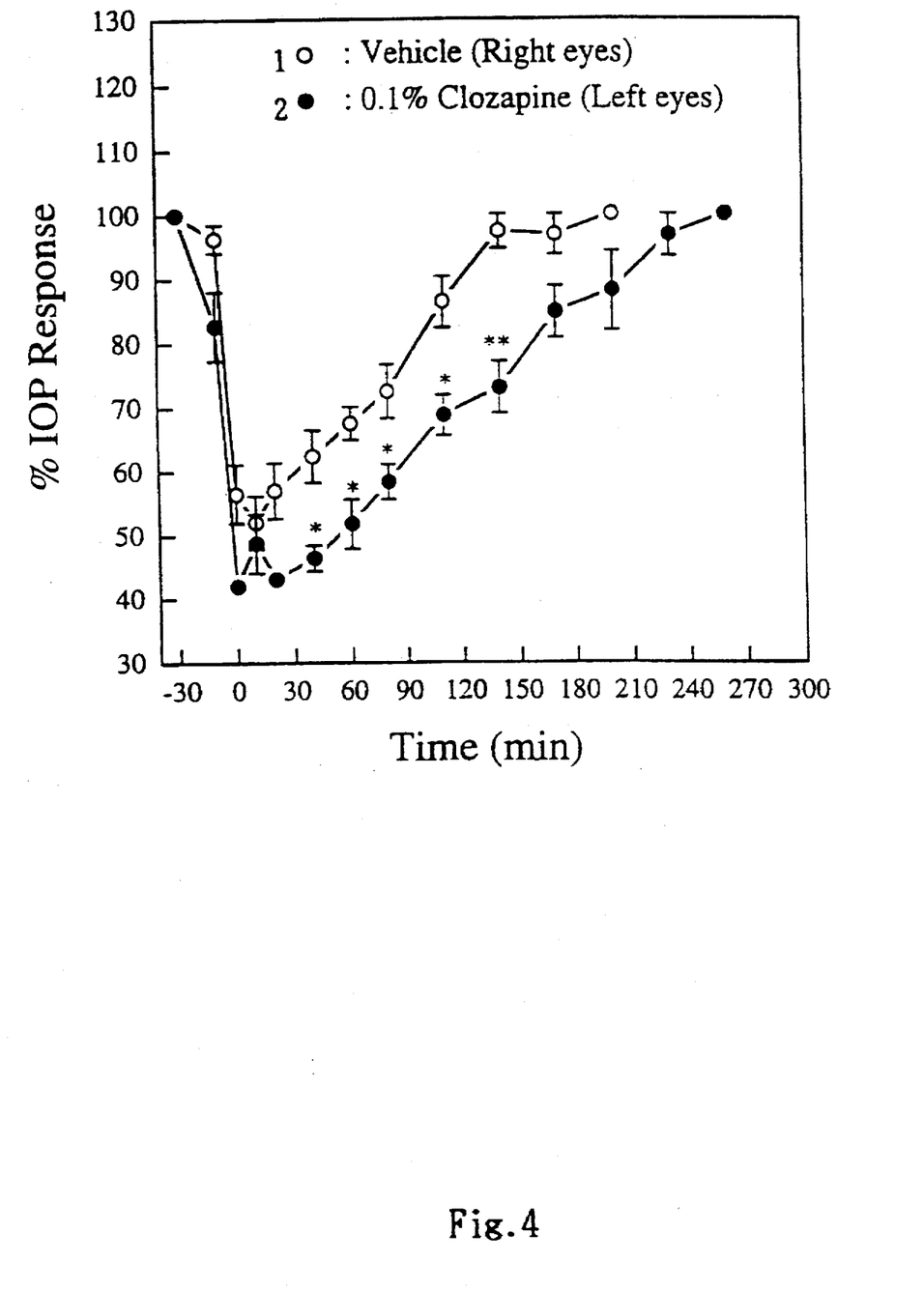
FIG. 4 is a graph showing that clozapine was able to decrease the intraocular pressure (IOP) in rabbits. The graph shows the effects of 0.1% clozapine in the rabbit IOP recovery model. Each point is the mean of 5 values and bars represent SEM. *:P<0.05; **:P<0.01 significantly different from the vehicle group. 1. Vehicle (right eye); 2. 0.1% Clozapine (left eye).
Figure 5:
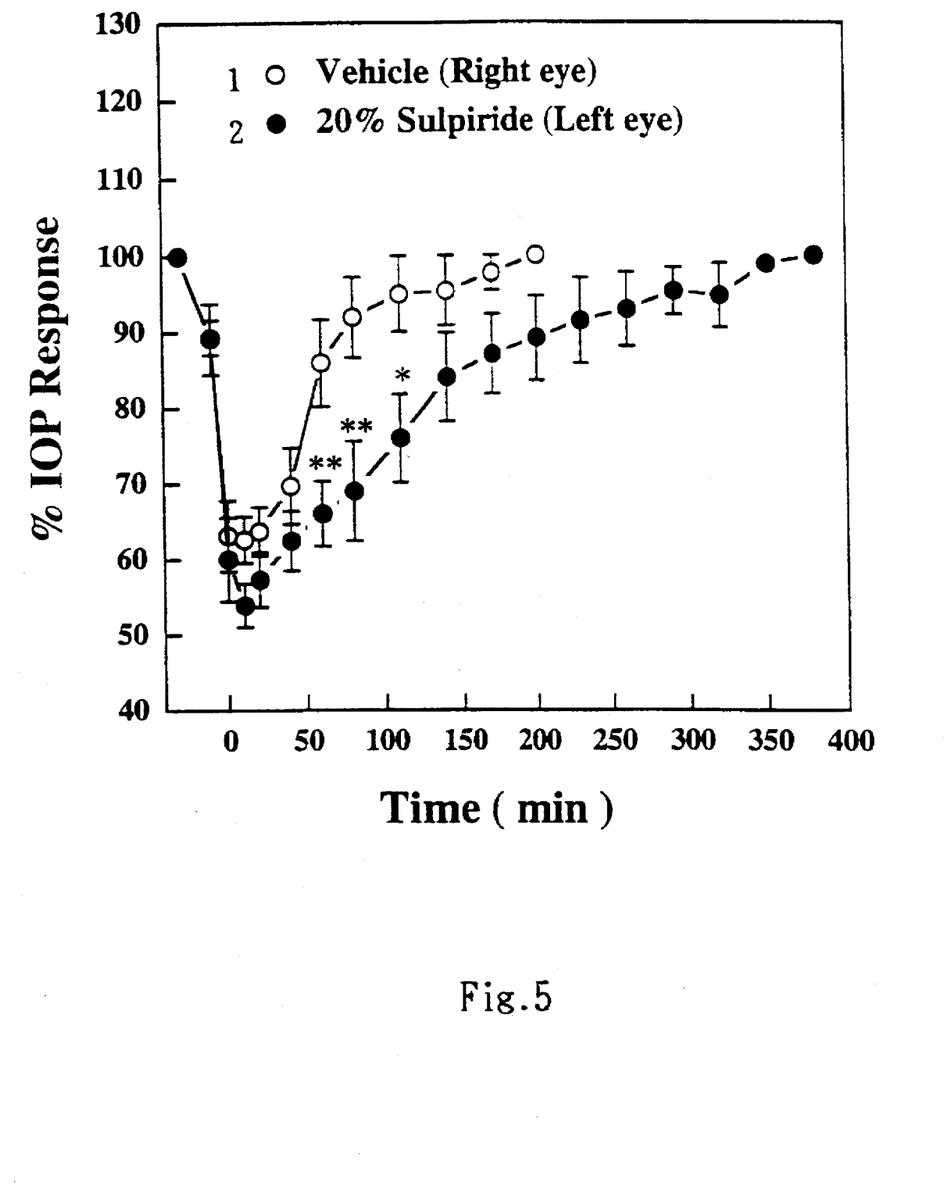
FIG. 5 is a graph showing that sulpiride was able to decrease the intraocular pressure (IOP) in rabbits. The graph shows the effects of 20% sulpiride in the rabbit IOP recovery model. *:P<0.05; **:P<0.01 significantly different from the vehicle group. 1. Vehicle (right eye); 2. 20% sulpiride (left eye).

As shown in FIG. 3 and FIG. 4, 0.25% and 0.1% dissolved Clozapine drop solution showed that it decreased IOP recovery time of rabbits more mildly. Although 0.5% Sulpiride didn't show a significant ability in decreasing lOP, it did so when the concentration was raised to 20% as shown in FIG. 5.

Measurement of the vasodilatation effect

A stunned guinea pig of 350–400 g was taken and an incision made at the arched place near the main artery. Then the main artery and all relevant tissue were taken out from the chest. They were put into saline immediately then cut into lengths of 2–4 MM. The main artery loop was installed on a parallel hook with 1 g tensile strength inside an organ container full of 10 ml saline. The composition of the saline in the container was NaCl 112 mM, KCl 5.0 Mm, $MgSO_4$ 1.2 mM, $NaHCO_3$ 25 mM, $KH_2PO_4$ 1.0mM, $CaCl_2$ 1.25 mM and glucose 11.5 mM. The organ container was kept at a temperature of 37° C. Then 95% oxygen and 5% carbon dioxide were mixed in.

The strength shown on the transducer was used as the tensile strength of the main artery loop. Before the experiment could be started, all the equipment had to be soaked in saline for one hour. The first procedure was to test the againsting α-adrenergic function, so as to test the biggest muscle contraction function of $10^{-6}M$ phenylephrine. Clozapine was used to release its contraction.

According to Godfraing's report in 1969 Br. J. Pharmacol vol. 36,549–560, depolarizing solution of high concentrated $k^+$ would cause the main artery's contraction. The Depolarizing solution of high concentrated $k^+$ was composed of NaCl 17 mM, KCl100 mM, $MgSO_4$ 1.2 mM, $NaHCO_3$ 25 mM, $KH_2PO_4$ 1.0 mM, $CaCl_2$ 1.25 mM and glucose 11.5 mM. Clozapine was added to the organ container when the biggest contraction occurred, which reduced the main artery's contraction.

Result

Figure 6:
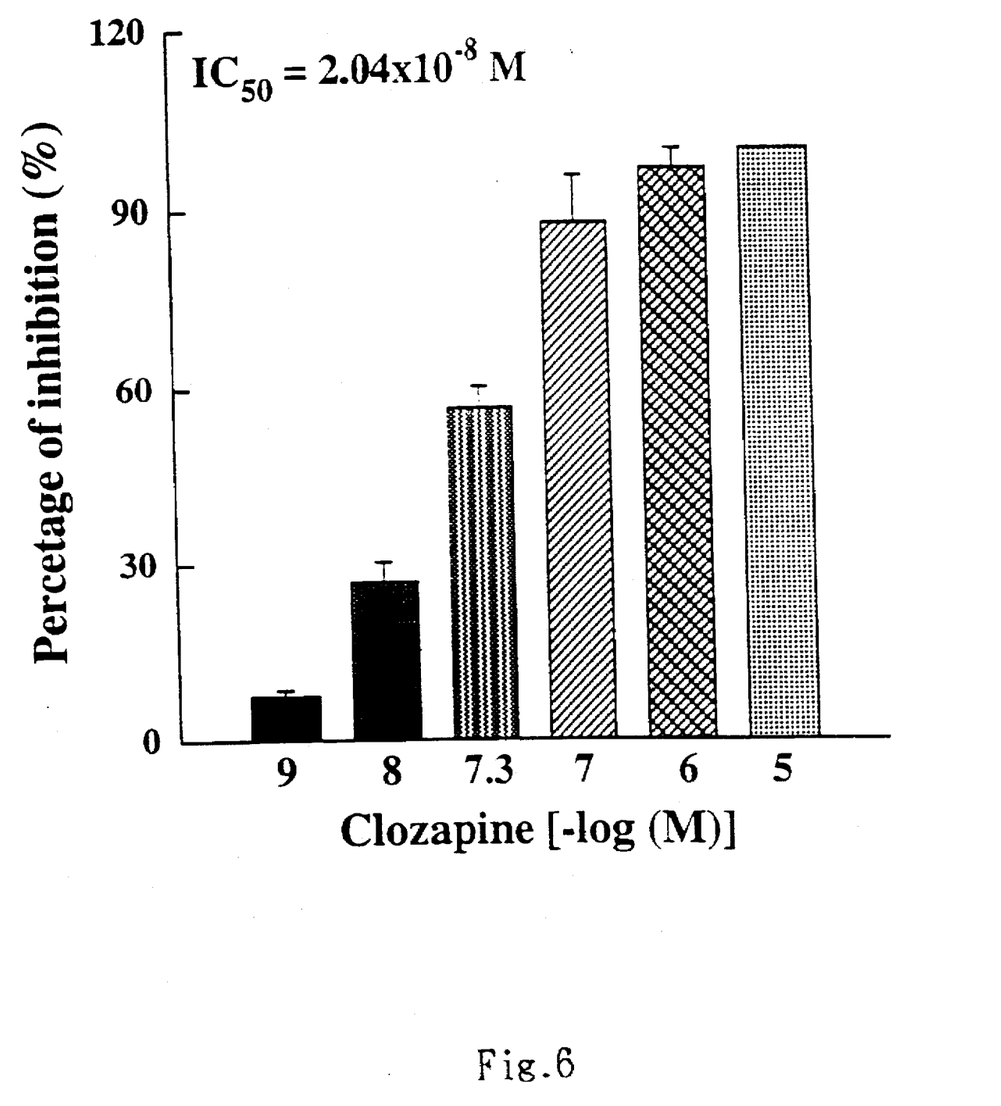
FIG. 6 is a graph showing clozapine's restraint ratio to phenylephrine.
Figure 7:
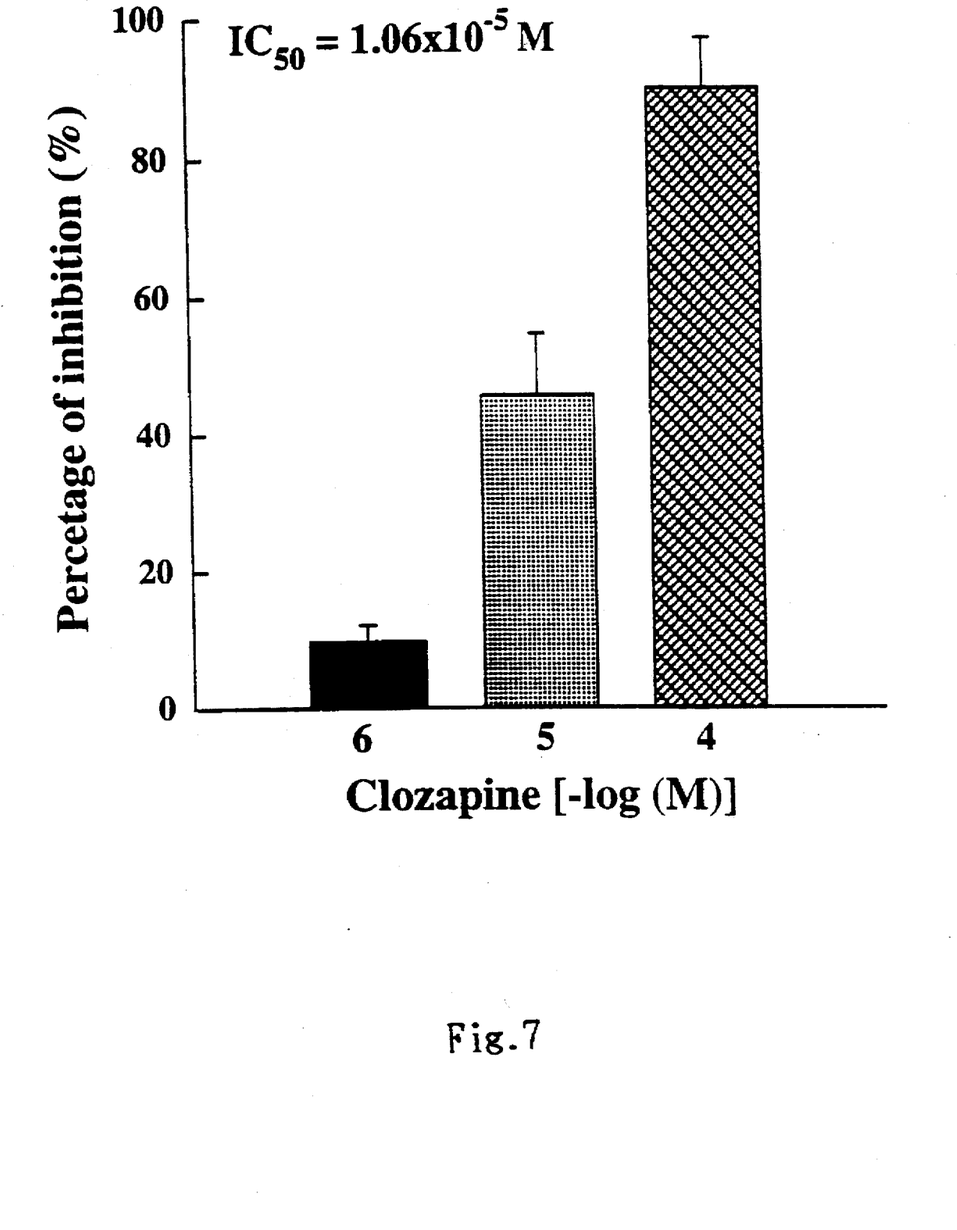
FIG. 7 is a graph showing clozapine's restraint ratio to phenylephrine.

The test result of the vasodilation effect is shown as FIG. 6. When the concentration of Clozapine increases, it could effectively restrain contraction caused by phenylephrine. The estimated $IC_{50}$ value is $2\times10^{-8}M$. Clozapine also could restrain contraction caused by $K^+$, restrain the calculated contraction caused by $Ca^{++}$. As the $IC_{50}$ value shown in FIG. 7, Clozapine could restrain the constriction caused by phenylephrine-induced $Ca^{++}$ mobilization.

Clozapine increases ocular blood flow

The experiment format of increasing blood flow used was following the method what Chiou, G. C. Y. & Co. had reported in 1993 J. Ocular Pharmacol vol.9 pp.179–185.

We chose New Zealand white rabbits weighing 2.5–3.0 kg anesthetized by injecting 35 mg/kg ketamine and 5 mg/kg xylazine. Half of the initial dose was given after one hour to maintain adequate anesthesia. The left ventricle was cannulated through the right carotid artery to inject colored microspheres(the diameter was 15), and the femoral artery was cannulated for blood collection. 0.1% and 0.25% Clozapine solution or vehicle were instilled in the eyes. The ocular blood flow of a ocular hypertensive rabbit was measured with colored microspheres at 0, 30, 60, 120, and 180 min intervals thereafter. After one minute of each injection of microspheres, blood samples were taken from the femoral artery immediately as a reference. The blood samples were collected in a tube with heparin and the volume of each was recorded.

After injecting the last microspheres and collecting the last blood samples, the animals were sacrificed and the eyes were dissected. The retina, choroid, iris and ciliary body were all weighted.

The samples were processed by an American company E-Z Trac and the counting method of microsphere was provided by them too. Tissue samples were put in microfuge tubes with tissue (blood) digest reagent I, and the caps were sealed tightly. They were heated at 95° C. for 15 minutes, then vortexed in a vortexer for 30 minutes. The tissue samples were heated and vortexed until they were completely dissolved. While the tissue samples were still with heat, they were added with Tissue (Blood) Digest Reagent II, and the caps were sealed. They were vortexed and the tubes were centrifuged to settle the microspheres to the bottom of the tubes. Then the supernatant was removed and the pellet was resuspended in a Microsphere Counting Reagent of precise volume. The number of various colored microspheres were counted with an emocytometer.

Hemolysis Reagent was added to the blood samples. Then they were vortexed and centrifuged for 30 minutes in a low revolution, Supernatant was removed, and Tissue (Blood) Digest Reagent I was added. As followed in the previously stated procedure to test tissue samples, the number of colored microspheres were counted.

The blood flow of each tissue at a certain time point was able to be calculated with the following equation:

$$Qm = (Cm \times Qr)/Cr$$

Qm: the blood flow of a tissue, the unit is μl/min/mg

TABLE 1

Effects of clozapine on rabbit ocular blood flow
Blood Flow (μl/min/mg tissue)

| Tissue | Treatment | 0 min | 30 min | 60 min | 120 min | 180 min |
|---|---|---|---|---|---|---|
| iris | Control | 0.61 ± 0.01 | 0.54 ± 0.01 | 0.57 ± 0.02 | 0.50 ± 0.05 | 0.52 ± 0.07 |
|  | 0.1% | 0.59 ± 0.03 | 0.67 ± 0.02* | 0.98 ± 0.08 | 0.77 ± 0.05 | 0.56 ± 0.04* |
|  | 0.25% | 0.57 ± 0.02 | 0.72 ± 0.02 | 1.11 ± 0.08* | 1.46 ± 0.13* | 0.72 ± 0.05* |
| ciliary body | Control | 0.60 ± 0.01 | 0.48 ± 0.02 | 0.50 ± 0.01 | 0.44 ± 0.03 | 0.45 ± 0.04 |
|  | 0.1% | 0.59 ± 0.02 | 0.67 ± 0.04 | 1.27 ± 0.02 | 0.91 ± 0.10 | 0.52 ± 0.01* |
|  | 0.25% | 0.58 ± 0.01 | 0.71 ± 0.02* | 1.27 ± 0.04* | 1.37 ± 0.06* | 0.77 ± 0.01* |
| retina | Control | 0.058 ± 0.002 | 0.050 ± 0.002 | 0.052 ± 0.001 | 0.050 ± 0.002 | 0.051 ± 0.001 |
|  | 0.1% | 0.056 ± 0.001 | 0.060 ± 0.002 | 0.078 ± 0.004 | 0.059 ± 0.001 | 0.049 ± 0.002 |
|  | 0.25% | 0.060 ± 0.002 | 0.065 ± 0.005* | 0.152 ± 0.010* | 0.075 ± 0.014* | 0.058 ± 0.002* |
| choroid | Control | 3.22 ± 0.07 | 3.14 ± 0.09 | 3.16 ± 0.11 | 3.14 ± 0.11 | 2.16 ± 0.10 |
|  | 0.1% | 3.15 ± 0.02 | 4.18 ± 0.36 | 4.90 ± 0.33 | 3.16 ± 0.09 | 2.14 ± 0.03 |
|  | 0.25% | 3.10 ± 0.01 | 4.98 ± 0.25* | 6.04 ± 0.19* | 4.41 ± 0.31* | 2.70 ± 0.13* |

All values represent mean ± SEM with N = 9. Stars indicate statistical significance at P <0.05 between control and treated.

Cm: the total number of tissue microsphere per mg

Qr: the flow rate of blood sample, the unit is μl/min

Cr: the total number of microsphere of referenced blood sample.

Result

As shown in Table 1 of ocular blood flow in retina, choroid, iris and ciliary body. No matter if the clozapine was of 0.1, 0.25% or 0.5% they showed significant increases in ocular blood flow from 30 to 180 minutes.

Example 1 Clozapine drop solution 0.9% NaCl
20% Clozapine
dilute $Na_2HPO_4$
2.5% hydroxypropyl β-cyclodextrin
carboxymethycellulose

Example 2 Sulpiride drop solution

20% Sulpiride
propyleneglycol (20%)
0.9% NaCl

Example 3 Clozapine drop solution 0.25% Clozapine
0.9 NaCl
dilute HCl

Example 4 Clozapine drop solution 0.1% Clozapine
0.9 NaCl
dilute HCl

Explanation of Table

Table 1 depicts the effects of Clozapine on rabbit ocular blood flow, Clozapine increases ocular blood flow in the iris, ciliary body, retina and choroid respectively. All values represent mean ±SEM with N=9. Stars indicate statistical significance at P<0.05 between control and treated.

What our claims are:

1. A method for treating glaucoma, decreasing intraocular pressure and increasing blood flow of the retina comprising the step of:
   administering to a patient in need thereof, an effective dose of an ocular pharmaceutical composition comprising a member selected from the group consisting of clozapine and sulpiride and a pharmaceutically acceptable carrier.

2. A method for treating glaucoma, decreasing intraocular pressure and increasing blood flow of the retina as defined in claim 1 comprising the step of:
   administering to a patient in need thereof, an effective dose of an ocular pharmaceutical composition comprising sulpiride and a pharmaceutically acceptable carrier.

3. A method for treating glaucoma, decreasing intraocular pressure and increasing blood flow of the retina as defined in claim 1 comprising the step of:
   administering to a patient in need thereof, an effective dose of an ocular pharmaceutical composition comprising clozapine and a pharmaceutically acceptable carrier.

4. A method for treating glaucoma, decreasing intraocular pressure and increasing blood flow of the retina as defined in claim 1 comprising the step of:
   administering to a patient in need thereof, an effective dose of the ocular pharmaceutical composition wherein the ocular pharmaceutical composition is in the form of an ointment or a drop solution.

5. A method for treating glaucoma, decreasing intraocular pressure and increasing blood flow of the retina as defined in claim 2 wherein the ocular pharmaceutical composition is in the form of an ointment.

6. A method for treating glaucoma, decreasing intraocular pressure and increasing blood flow of the retina as defined in claim 2 wherein the ocular pharmaceutical composition is in the form of a drop solution.

7. A method for treating glaucoma, decreasing intraocular pressure and increasing blood flow of the retina as defined in claim 5 wherein the ointment further comprises a member selected from the group consisting of white petrolatum, mineral oil and water-free sheep oil.

8. A method for treating glaucoma, decreasing intraocular pressure and increasing blood flow of the retina as defined in claim 6 wherein the drop solution further comprises a member selected from the group consisting of propylene glycol, sodium chloride, boric acid, alkaline mineral acid, sodium phosphate, hydroxypropyl β cyclodextrin, carboxymethylcellulose and chlorobutanol.

9. A method for treating glaucoma, decreasing intraocular pressure and increasing blood flow of the retina as defined in claim 3 wherein the ocular pharmaceutical composition is in the form of an ointment.

10. A method for treating glaucoma, decreasing intraocular pressure and increasing blood flow of the retina as defined in claim 3 wherein the ocular pharmaceutical composition is in the form of a drop solution.

11. A method for treating glaucoma, decreasing intraocular pressure and increasing blood flow of the retina as defined in claim 9 wherein the ointment further comprises a member selected from the group consisting of white petrolatum, mineral oil and water-free sheep oil.

12. A method for treating glaucoma, decreasing intraocular pressure and increasing blood flow of the retina as defined in claim 10 wherein the drop solution further comprises a member selected from the group consisting of sodium chloride, boric acid, alkaline mineral acid, sodium phosphate, hydroxypropyl β cyclodextrin, carboxymethylcellulose and chlorobutanol.

13. A method for treating glaucoma, decreasing intraocular pressure and increasing blood flow of the retina as defined in claim 2 wherein the ocular pharmaceutical composition contains about 20% sulpiride.

14. A method for treating glaucoma, decreasing intraocular pressure and increasing blood flow of the retina as defined in claim 3 wherein the ocular pharmaceutical composition contains from about 0.1% to about 0.5% clozapine.

15. A method for treating glaucoma, decreasing intraocular pressure and increasing blood flow of the retina as defined in claim 8 wherein the ocular pharmaceutical composition contains about 20% sulpiride.

16. A method for treating glaucoma, decreasing intraocular pressure and increasing blood flow of the retina as defined in claim 12 wherein the ocular pharmaceutical composition contains from about 0.1% to about 0.5% clozapine.

17. A method for treating glaucoma, decreasing intraocular pressure and increasing blood flow of the retina as defined in claim 7 wherein the ocular pharmaceutical composition contains about 20% sulpiride.

18. A method for treating glaucoma, decreasing intraocular pressure and increasing blood flow of the retina as defined in claim 11 wherein the ocular pharmaceutical composition contains from about 0.1% to about 0.5% clozapine.

19. A method for treating glaucoma, decreasing intraocular pressure and increasing blood flow of the retina comprising the step of:

administering to an animal in need thereof, an effective dose of an ocular pharmaceutical composition comprising a member selected from the group consisting of clozapine and sulpiride and a pharmaceutically acceptable carrier.

* * * * *